United States Patent
Kuntaegowdanahalli et al.

(10) Patent No.: US 9,427,565 B2
(45) Date of Patent: Aug. 30, 2016

(54) MODULAR MULTI-CHANNEL INLINE CONNECTOR SYSTEM

(71) Applicants: Sathyakumar S. Kuntaegowdanahalli, Miami, FL (US); James J. Abbas, Scottsdale, AZ (US); Ranu Jung, Miami Beach, FL (US); Kenneth Horch, Fountain Hills, AZ (US)

(72) Inventors: Sathyakumar S. Kuntaegowdanahalli, Miami, FL (US); James J. Abbas, Scottsdale, AZ (US); Ranu Jung, Miami Beach, FL (US); Kenneth Horch, Fountain Hills, AZ (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 14/073,437

(22) Filed: Nov. 6, 2013

(65) Prior Publication Data
US 2014/0128951 A1    May 8, 2014

Related U.S. Application Data

(60) Provisional application No. 61/723,524, filed on Nov. 7, 2012.

(51) Int. Cl.
*A61N 1/05* (2006.01)
*A61N 1/36* (2006.01)

(52) U.S. Cl.
CPC ............... *A61N 1/05* (2013.01); *A61N 1/0504* (2013.01); *A61N 1/0551* (2013.01); *A61N 1/36017* (2013.01)

(58) Field of Classification Search
CPC .... A61N 1/05; A61N 1/0504; A61N 1/0551; A61N 1/36017

USPC ................................................. 607/2, 60, 116
See application file for complete search history.

(56) References Cited

U.S. PATENT DOCUMENTS

| | | | | |
|---|---|---|---|---|
| 4,819,662 | A * | 4/1989 | Heil, Jr. ............... | A61N 1/0568 607/116 |
| 5,354,326 | A * | 10/1994 | Comben et al. ............. | 607/115 |
| 5,417,719 | A * | 5/1995 | Hull et al. ...................... | 607/46 |
| 5,468,996 | A * | 11/1995 | Chan et al. .................... | 257/723 |
| 5,507,303 | A * | 4/1996 | Kuzma ......................... | 128/899 |
| 5,701,895 | A * | 12/1997 | Prutchi et al. ................ | 600/300 |
| 5,741,322 | A * | 4/1998 | Mehmanesh et al. ........ | 607/129 |
| 5,782,645 | A * | 7/1998 | Stobie et al. .................. | 439/289 |
| 5,782,892 | A * | 7/1998 | Castle et al. .................... | 607/37 |
| 6,725,096 | B2 * | 4/2004 | Chinn et al. ................... | 607/115 |
| 7,343,204 | B2 * | 3/2008 | Schulman ................ | A61N 1/05 439/909 |
| 7,548,788 | B2 * | 6/2009 | Chinn et al. .................. | 607/117 |
| 8,239,042 | B2 * | 8/2012 | Chinn et al. .................. | 607/117 |
| 8,504,172 | B2 * | 8/2013 | Chinn et al. .................. | 607/117 |
| 8,527,054 | B2 | 9/2013 | North | |

(Continued)

*Primary Examiner* — Christopher A Flory
(74) *Attorney, Agent, or Firm* — Marshall, Gerstein & Borun LLP (57) ABSTRACT

A modular multi-channel inline connector system that connects an implanted electrode within a body of an organism, such as the human body, with a device located external to or implanted within the body. The modular multi-channel inline system comprises of a first lead operatively connected to the implanted electrode and to a first connector portion. A second lead is operatively connected to a second connector portion and operatively connected to the device. One of the first and second connector portions comprises a male connector and the other of the first and second connector portions comprises a female connector. The first and second connector portions are arranged to connect with each other and to be operatively located embedded within the body.

14 Claims, 5 Drawing Sheets

(56) References Cited

U.S. PATENT DOCUMENTS

| | | | |
|---|---|---|---|
| 8,545,261 B2* | 10/2013 | Litzler et al. | 439/502 |
| 8,660,658 B2* | 2/2014 | Walsh | A61N 1/36032 381/312 |
| 2002/0143376 A1 | 10/2002 | Chinn et al. | |
| 2003/0050680 A1* | 3/2003 | Gibson | A61N 1/05 607/116 |
| 2003/0199948 A1* | 10/2003 | Kokones et al. | 607/117 |
| 2005/0131506 A1* | 6/2005 | Rezai et al. | 607/117 |
| 2005/0283203 A1* | 12/2005 | Flaherty et al. | 607/48 |
| 2006/0004421 A1* | 1/2006 | Bennett et al. | 607/41 |
| 2006/0004429 A1* | 1/2006 | Mrva et al. | 607/116 |
| 2006/0030918 A1* | 2/2006 | Chinn et al. | 607/117 |
| 2006/0271136 A1* | 11/2006 | Wojciechowicz | A61N 1/05 607/116 |
| 2008/0071321 A1* | 3/2008 | Boggs et al. | 607/39 |
| 2008/0071322 A1* | 3/2008 | Mrva et al. | 607/41 |
| 2008/0132969 A1* | 6/2008 | Bennett et al. | 607/41 |
| 2008/0161874 A1* | 7/2008 | Bennett et al. | 607/39 |
| 2009/0240314 A1* | 9/2009 | Kong et al. | 607/116 |
| 2009/0247018 A1 | 10/2009 | Kast et al. | |
| 2009/0248096 A1* | 10/2009 | Chinn et al. | 607/2 |
| 2010/0137928 A1* | 6/2010 | Duncan | A61N 1/05 607/5 |
| 2010/0324640 A1* | 12/2010 | Bauer | A61N 1/05 607/116 |
| 2011/0144468 A1* | 6/2011 | Boggs et al. | 600/373 |
| 2011/0245893 A1* | 10/2011 | McGiboney | B23K 26/32 607/72 |
| 2012/0167385 A1* | 7/2012 | McGiboney | A61N 1/0551 29/846 |
| 2012/0276767 A1* | 11/2012 | Chinn et al. | 439/310 |
| 2012/0283806 A1* | 11/2012 | Troosters | A61N 1/3752 607/116 |
| 2012/0290055 A1* | 11/2012 | Boggs, II | 607/116 |
| 2013/0023973 A1* | 1/2013 | Richard | A61N 1/375 607/116 |
| 2013/0238066 A1* | 9/2013 | Boggs et al. | 607/116 |
| 2014/0163664 A1* | 6/2014 | Goldsmith | 623/1.11 |
| 2015/0142092 A1* | 5/2015 | Vadlamudi | A61N 1/05 607/116 |

* cited by examiner

MODULAR MULTI-CHANNEL INLINE CONNECTOR SYSTEM

STATEMENT REGARDING FEDERALLY SPONSORED RESEARCH OR DEVELOPMENT

This invention was made with government support under Award or Contract No. N66001-12-C-4195 awarded by the Defense Advanced Research Projects Agency (DARPA). The government may have certain rights in the invention.

FIELD OF THE DISCLOSURE

The present disclosure relates generally to a modular multi-channel inline connector system to link electrodes to percutaneous leads or an implanted electrical device within an organism, such as a human body.

BACKGROUND

Neural interfaces technology is a rapidly growing segment of the medical device market. This technology mainly refers to devices that serve as an inter-connect between the stimulation/recording systems and the neuro-muscular tissue in the body. There currently are several known neuro-stimulation systems. Some notable neuro-stimulation systems include the cardiac pacemaker, cochlear implants, deep brain stimulation systems, spinal cord stimulation systems, gastric stimulation systems, vagal nerve stimulation systems, phrenic nerve stimulation systems, and others. Most of these systems include devices that are completely implantable into the human body, such as a patient.

Although not as prevalent as the neuro-stimulation systems, there are many non-implantable recording systems that can be used to record muscle and neural activity to control prostheses. There are also experimental systems being developed for implantable muscle and neural recordings.

In most of the neuro-stimulation/recording systems, it is common practice to test and calibrate the implanted electrodes, i.e., electrodes that are implanted into the body of the patient, prior to implanting the entire stimulator unit and/or recording unit into the patient's body. Specifically, the desired electrodes are first implanted at the target location in the patient's body and their efficacy is tested over a period of multiple days by using an external stimulator/recorder. After the trial period is over, if the electrodes function as intended, then the external connector is disconnected, and the leads are connected to an implantable stimulator/recorder that is programmed appropriately. On the other hand, if the electrodes do not function as intended, then only the electrodes need to be removed from the body instead of the whole implant. During the trial period, the leads from the implanted electrodes are connected to an external connector assembly through a percutaneous lead system. The stimulation/recording system plugs into the external connector assembly. In addition to being used during the trial period, the external connector assembly-percutaneous lead system can also be used to test novel electrode technology. This in particular usually requires the connector system to be functional for extended periods, such as from six months to one year.

Unfortunately, most known commercial percutaneous systems in the market today suffer from one or more of the following limitations:

a) they are often designed and used for a limited period, such as a trial period lasting over from two to seven days;
b) they often have high failure rates due to connector wear and tear, which is problematic because the electrodes will have to be replaced if the connector fails;
c) they often have high profile heights, particularly such systems that are designed for use as cranial implants; and/or
d) they are often not easily expandable.

Although multiple versions of inline connector and percutaneous systems have been developed and patented previously, none of them have a complete modular structure as the one presented in this document.

Hence a need exists to develop a modular, convenient and reliable connector system to link the stimulation/recording system (external non-implanted or internal implanted) to implanted electrodes. In one or more preferred forms, it would also be preferable that the connector system satisfy any one or more of the following conditions:

a) it may be designed to minimize trauma to the patient both from the surgical installation procedure and also from the day-to-day use;
b) all or at some parts of the connector system (external, internal and percutaneous section) may be designed so as to minimize the possibility of infection;
c) parts subject to wear and tear may be designed to be easily replaceable without need for surgical intervention;
d) external components may be designed to have a low profile height and should also occupy minimal footprint on the skin to minimize skin abrasions;
e) it may be designed to be easily expandable to accommodate additional electrodes; and/or
f) it may be designed to be modular to allow electrodes to be connected to either an external or an internal stimulation/recording system.

SUMMARY

According to some preferred aspects of the present disclosure, a connector assembly according to the teachings of the present disclosure optionally has a modular design. In some arrangements, this provides versatility to switch from a system architecture that has percutaneous leads to a system architecture with implanted electronics while being able to keep the same set of electrode contacts in place in the patient's body. In some arrangements, the modularity provides the ability to expand system capacity by adding more multi-channel electrodes to either the external connector system or the implanted electronics.

According to some preferred aspects of the present disclosure, the external connector assembly optionally is replaceable. In some arrangements, the percutaneous leads are detachable from the external connector assembly. In this embodiment, if the multi-pin connector on the external connector were to go bad, then the whole external connector assembly can be replaced without altering the implanted electrode contacts or the percutaneous leads.

According to some preferred aspects of the present disclosure, the external connector assembly optionally has a very low profile. In some arrangements, the whole assembly is made out of a flexible material so as to conform to the skin.

According to some preferred aspects of the present disclosure, the external connector setup may be easily expandable. For example, if additional electrodes need to be implanted in the nerve, then the current multi-pin connector assembly can be replaced with a new connector assembly box with more slots and a higher count multi-pin connector. This allows the current electrodes as well as the new set of electrodes to be used.

According to some preferred aspects of the present disclosure, the external connector configuration optionally greatly increases the number of connector mating cycles before system failure. In general, the smaller connectors tend to have limited mating cycle life. However, the modular structure according to the teachings of the present disclosure, in some arrangements, helps in compounding the mating life cycle. For example, if the proximal lead has a life of 100 mating cycles and the multi-pin commercial connector has a mating life of 500, then in theory, the whole ensemble could have a mating life of 50000 cycles.

According to some preferred aspects of the present disclosure, the inline connector system optionally has a very low profile. Existing technology for multi-channel systems either uses bulky multi-contact inline connectors or multiple single-contact inline connectors. In contrast, the inline connector system according to the teachings of the present disclosure, in some arrangements, has a much smaller profile.

According to some preferred aspects of the present disclosure, one end of the inline connector system optionally can be hardwired to multiple fine wires that are suitable for implantation directly into nerve fascicles. In contrast, existing technology for multi-channel systems use wires with diameters and materials that are not suitable for direct insertion into nerve fascicles.

Additional optional aspects and forms are disclosed, which may be arranged in any functionally appropriate manner, either alone or in any functionally viable combination, consistent with the teachings of the disclosure. These and other aspects and advantages will become apparent upon consideration of the following detailed description.

DETAILED DESCRIPTION

For the purpose of this disclosure, the term external shall refer to devices/components outside the body and the term implanted shall refer to devices/components installed inside the body.

In this disclosure, the connector system is explained for use with neural interfaces. However, the technology disclosed herein can be used in any application in which electrical or optical signals need to be transferred between a device outside the skin, i.e. external, to an implanted system (e.g. electrical/optical signal to activate an implanted system for targeted drug delivery).

The connector system design of this disclosure is described assuming longitudinal-intrafascicular electrodes (LIFE) implanted in the fascicles of the peripheral nerve. As such, the same design can be used to connect to any neural electrode such as Utah electrode array, cuff-electrode, tf-LIFE, etc., connected to nerves or other excitable tissue inside the body.

Figure 1:
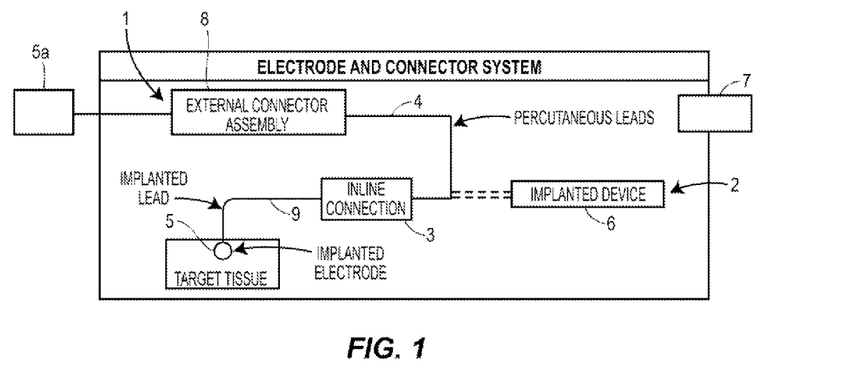
FIG. 1 shows components of an exemplary electrode and connector system according to the teachings of the present disclosure.

FIG. 1 shows high level schematic views of two system architectures of a modular multi-channel inline connector system for the technology of the present disclosure. One version is a multi-channel system 1 that uses an inline connector 3 to percutaneous leads 4 to link implanted electrode contacts 5 to external components 5a. The other version is a multi-channel system 2 that uses an inline connector 3 to link implanted electrode contacts 5 to an implanted device 6 that communicates (via RF or other transcutaneous link) to external components 7.

This presents a versatile system to transfer electrical activity between a device (in or out of the body) to a set of one or more electrodes implanted in tissue or other body organs from which electrical/optical activity can be recorded or stimulated.

As seen in FIG. 1, in a multi-channel system 1 with percutaneous leads, the connector has four parts: an external connector assembly 8, one or more percutaneous leads 4, one or more implanted leads 9, and an inline connection 3. The external connector assembly 8 serves to link the percutaneous lead(s) 4 with external equipment 5a, such as a stimulator or amplifier/recorder. The percutaneous lead(s) 4 have a multi-contact external connector on one end and an implantable multi-contact connector on the other. One connector could have one or more percutaneous leads. In the embodiment shown in FIG. 2, there is a multi-contact male connector 10 on the proximal end (external) and a female inline connector 11 on the distal (implanted) end, as shown in detail in FIGS. 5-10. The implanted leads 9 include a multi-contact connector 25 on one end and electrodes 5 on the other end. The inline connection 3 is the implantable multi-contact connection between implanted lead 9 and an extension (that may or may not be percutaneous) of the percutaneous lead 4. The connector setup will have as many inline connections as there are percutaneous leads 4. In the embodiment shown, the inline connection 3 is used to link the implanted lead 9 to the distal end of the percutaneous lead 4 inside the body.

In a multi-channel system 2 without percutaneous leads, the external connector assembly 8 and the percutaneous leads 4 are replaced by the implanted device 6. The implanted device 6 has multiple ports or docks for the multi-contact electrode leads similar to those described in U.S. Pat. No. 7,236,834, which is incorporated by reference in its entirety herein.

Figure 2:
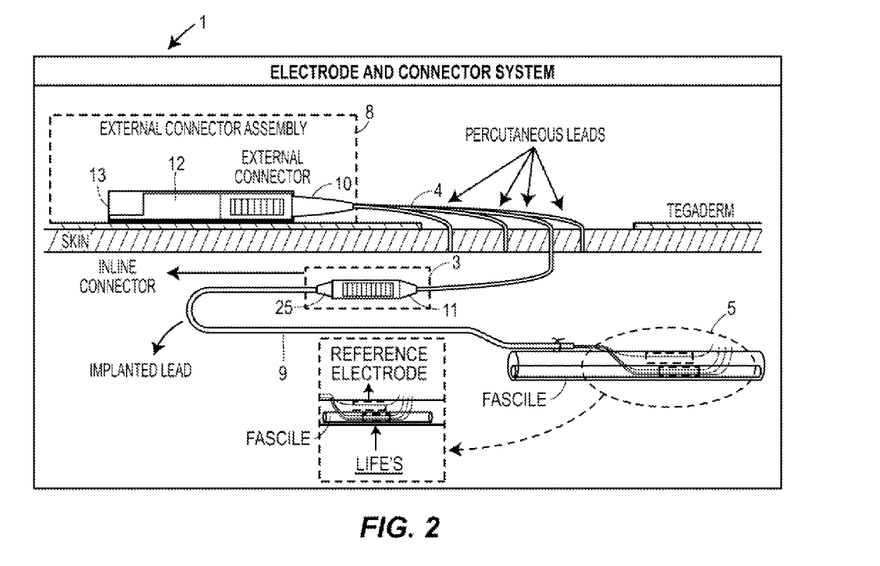
FIG. 2 is a schematic view of an exemplary external connector assembly according to the teachings of the present disclosure.

FIG. 2 shows a more detailed schematic of the entire electrode-connector system of FIG. 1 with implanted and external parts including an embodiment with percutaneous leads, corresponding to the system 1. Each part of this embodiment of the connector system 1 shown in FIG. 2 is explained in detail hereinafter with reference to FIGS. 3-10.

Figure 3:
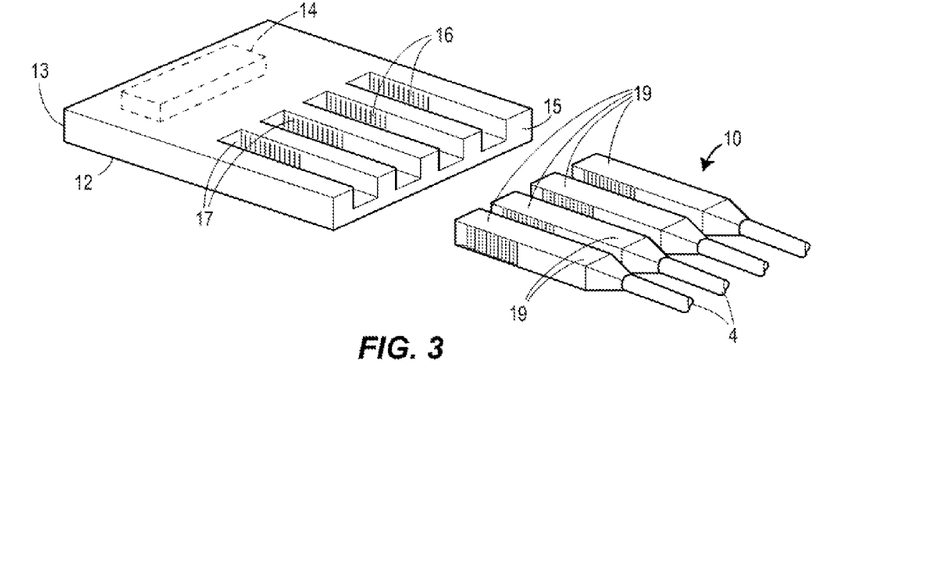
FIG. 3 is a schematic view of the external connector assembly according to the teachings of the present disclosure.

FIG. 3 shows a schematic of an external connector assembly 8 of FIG. 2, along with the mating percutaneous leads 4. The external connector assembly 8 includes a central core 12 covered by an outer shell (not shown in FIG. 3). The central core 12 is made up of a printed circuit board (PCB) 13, which may be flexible or other, with a multi-pin connector 14, such as a Micro PSM Series 32-pin female connector from Omnetics, on one end. The other end 15 has multiple columns of contacts 16 molded into slots 17 as shown in the schematic. The connections between the multi-pin connector 14 and the contacts are made on the PCB 13.

Figure 4:
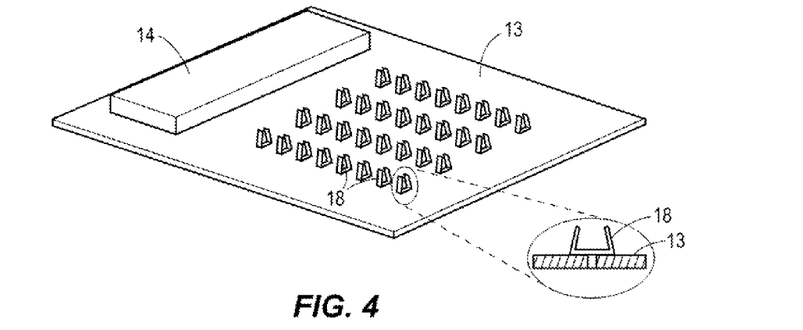
FIG. 4 is a schematic of a printed circuit board with contact pins soldered onto it according to the teachings of the present disclosure.

FIG. 4 shows a schematic of just the PCB 13 of FIG. 3 with contact pins 18 and the multi-pin connector 14 soldered to it. As seen in FIG. 4, the contact pins 18 are bent inward to ensure good contact with the proximal end 19 of the percutaneous lead 4.

The PCB 13 can be made of FR4 material and is RoHS compliant. A preferred thickness of the PCB 13 is about 787 µm. The contact pins 18 are typically made of stainless steel, nickel-plated stainless steel, gold-plated beryllium copper, titanium, tantalum or noble metals such as platinum or platinum/iridium. The contact pins 18 are preferably soldered onto the board 13 using lead-free solder. Alternatively, the contact pins 18 can also be welded to the pads on the PCB. The plastic mold preferably is an electrical insulator. It is preferably made out of a bio-compatible material such as urethane, silicone, polytetrafluroethylene (PTFE), epoxy, poly-sulphone or similar materials. The top and bottom lids of the outer shell can also be made of material listed above. The lids can either be screwed into the molded plastic or slid into a groove in the molded plastic.

Figure 5:
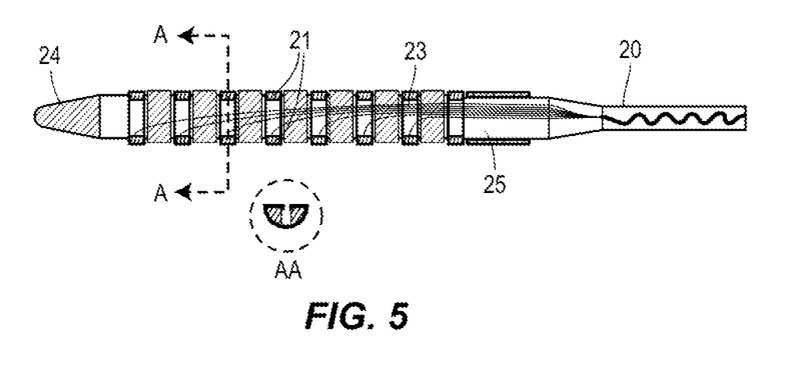
FIG. 5 is a schematic view of a proximal connector on a percutaneous lead according to the teachings of the present disclosure.

FIG. 5 shows a schematic of the proximal end (external) 19 of the percutaneous lead 4. The body 24 of the proximal lead 4 includes an outer tube 20 with an outer diameter between 1.8 mm to 2 mm and an inner diameter of between 1.2 mm to 1.5 mm. The body includes grooves 22 to fit the contact pins 21 as shown in FIG. 5. The contact pins 21 are manufactured separately and can be positioned in the grooves 22 by pushing the contact pins 21 onto the grooves 22. The contact pin 21 preferably fits in snuggly with the groove 22. Additionally one could also glue the contact pins 21 to the grooves 22 using a medical grade adhesive. Each contact pin 21 is soldered to a lead wire 23 which extends out of the lead body 24 through a hollow channel 25 at the center as shown in FIG. 5. Finally the body 24 of the lead is sealed on the top side (FIG. 5 shows the top view without the top lid 35) by gluing a plastic lid 35, preferably to the body 24.

The contact pins 21 are preferably made of stainless steel, nickel-plated stainless steel, gold-plated beryllium copper, titanium, tantalum or noble metals such as platinum or platinum/iridium. The contact pins 21 preferably are soldered onto the board using lead-free solder. Alternatively, the contact pin 21 can also be welded to the pads on the PCB. The body 24 preferably is a plastic mold and preferably is an electrical insulator. The body 24 is preferably made out of a biocompatible material such as urethane, silicone, polytetrafluroethylene (PTFE), epoxy, poly-sulphone or similar materials. The wires 23 in the lead 4 can be made of any biocompatible material such as stainless steel, platinum, platinum-iridium. Each wire 23 preferably is insulated using biocompatible material such as PTFE or PFA. The ensheathing tube (outer tube) 20 is preferably made of a medical grade tubing material, such as silicone.

Each proximal end 19 of the percutaneous lead 4 is mated with the external connector assembly 8 by lining the lead 4 directly on top of the slot 17 such that the "alignment grooves" 22 line up, and then by pushing it down. Once all the leads 4 are placed in the slots 17, the top lid 35 is screwed in. The grooves 22 on the lead 4 prevent the lead from sliding out of the slot 17 horizontally. The top lid 35 holds the lead 4 in place in the slot 17 from the top.

Figure 6:
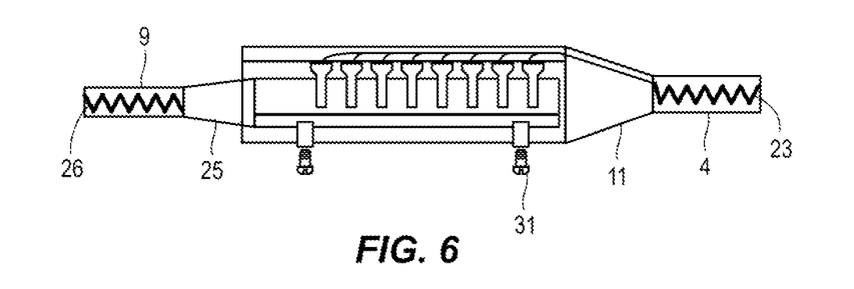
FIG. 6 is a schematic view of the inline connection between the percutaneous lead and an implanted lead according to the teachings of the present disclosure.

FIG. 6 contains a schematic showing the inline connection 3 between the implanted lead 9 and the percutaneous lead 4, including a male connector 25 and a female connector 11. The implanted lead 9 has LIFE wires 26 on one end and a male connector lead 25 on the other end. As mentioned previously, the percutaneous lead 4 has a male connector 10 external to the body and a female hollow connector 11 inside the body. Subsequent paragraphs provide a short description of optional arrangements for the male and female parts 25, 11 of the inline connection 3.

Figure 7:
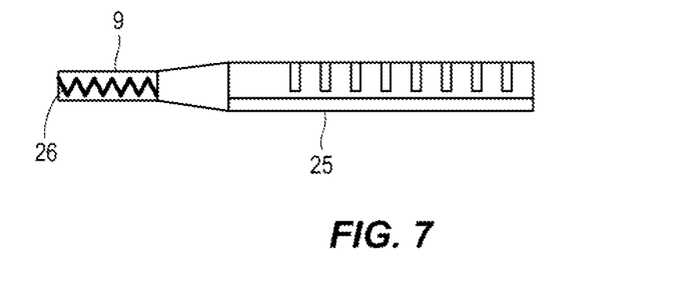
FIG. 7 is a schematic view of a male connector on the distal end of the implanted lead according to the teachings of the present disclosure.
Figure 8:
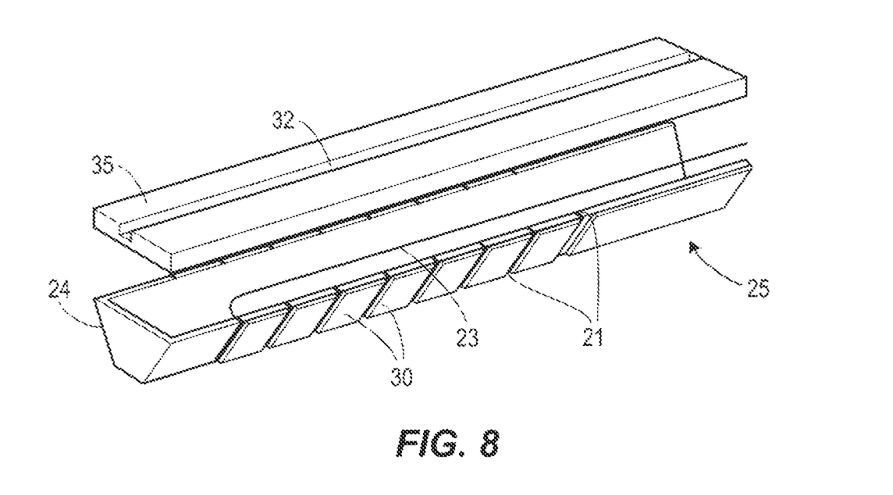
FIG. 8 is an isometric view of the male connector on the implanted lead according to the teachings of the present disclosure.
Figure 9:
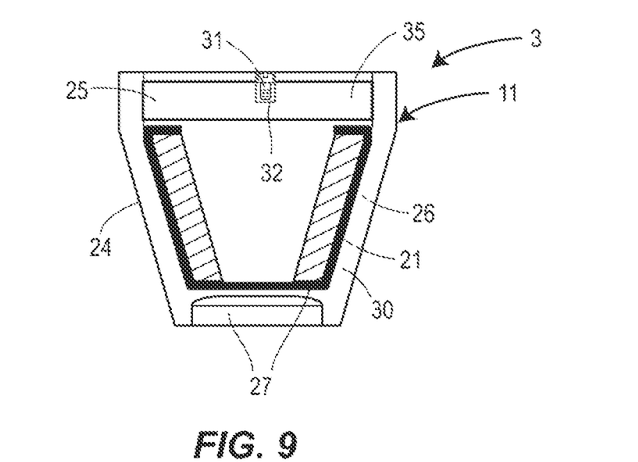
FIG. 9 is a cross-sectional view of the male connector of FIG. 8 showing the contact point according to the teachings of the present disclosure.

FIG. 7 contains a schematic of the male end 25 of the connector 3. The design for this connector is the same as the proximal end 19 of the percutaneous lead 4 except for the alignment groove 32 on top. In case of LIFE electrodes, the Pt-Ir LIFE wires are soldered/welded directly onto the contact as explained previously. Additionally, all the materials used in this case are preferably implant grade. FIG. 8 contains an isometric view of the male connector lead 25 and FIG. 9 shows the cross sectional view of the same.

Figure 10:
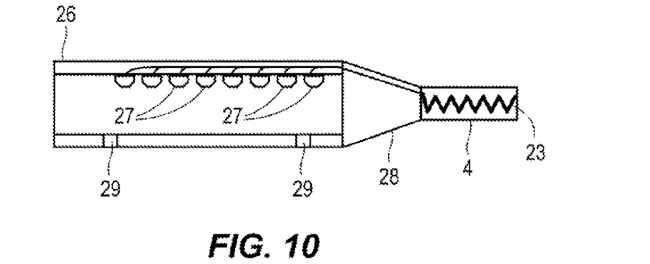
FIG. 10 is a schematic view showing a female connector on the distal end of the percutaneous lead according to the teachings of the present disclosure.

FIG. 10 contains a schematic showing the side, cross-sectional view of the female connector 11. The female connector 11 includes a hollow tube, with pins 27 attached on the top. The percutaneous lead wires 23 are soldered to individual pins 27 and the connector body 26 is molded around it by using the pins 27 as an insert in the mold. The tapered end 28 provides strain relief. The body 26 also has threaded screw holes 29 on the bottom side as seen in FIG. 10. The screw holes 29 aid in guiding the male lead as it is inserted.

To mate and secure the male lead 25 to the female lead 11, the male lead 25 is inserted all the way into the female lead 11, and the female lead 11 is screwed with anchor screws 31 in to make a tight, sealed contact.

The contact pins 27 are preferably made of stainless steel, nickel-plated stainless steel, titanium, or noble metals such as platinum or platinum/iridium. The plastic mold forming the body 26 is preferably an electrical insulator. The plastic mold forming the body 26 may be made out of a bio-compatible material such as urethane, silicone, polytetra-fluroethylene (PTFE), epoxy, poly-sulphone or similar materials. Both the male and female leads 25, 11 are lined with silicone pads (isolation pads) 30 to prevent body fluids from entering the connector 3 and shorting the leads 9, 4.

Figure 11:
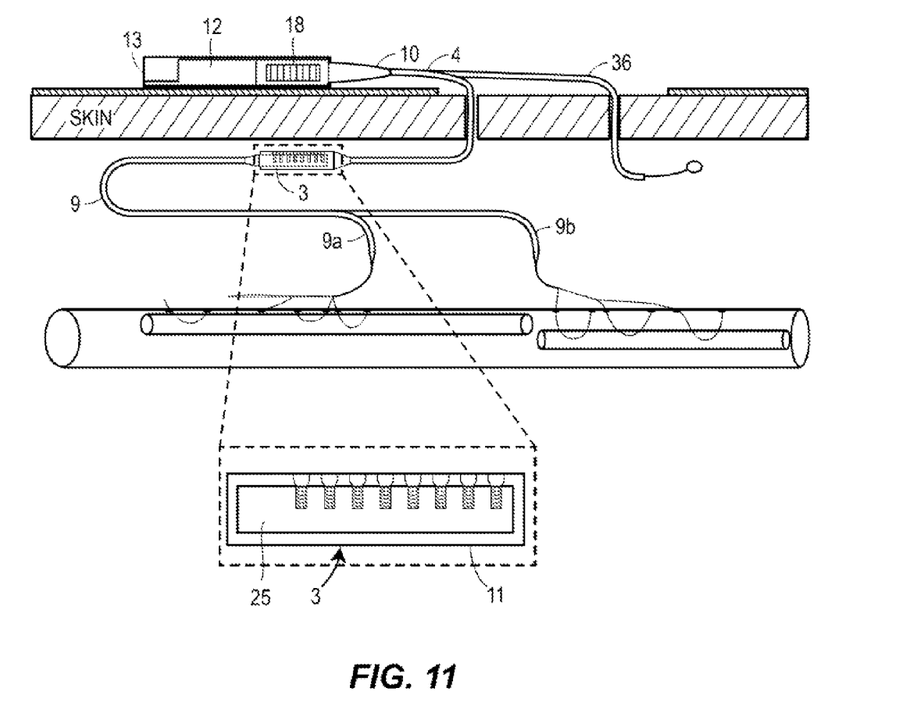
FIG. 11 is a schematic of the inline connector system of FIG. 2 in another arrangement including a ground electrode embedded inside the body.

FIG. 11 shows the multi-channel system 1 arranged with a ground electrode 36 connected by a percutaneous lead 4 to the external connector assembly 8. Further, the implanted lead 9 includes a plurality of different parallel lead portions 9a, 9b. At one end of the lead 9, the lead portions 9a, 9b are bundled together in a single bundle. The bundle is connected to the inline connector 3. At the other end of the lead 9, the lead portions 9a, 9b are separated so as to be able to connect different electrode contacts 5 to different spaced apart regions, such as different and/or spaced apart nerve and/or muscle groups.

In general terms, a system according to the teachings of the present disclosure can be used in any application where electrical signals need to be passed between an external system and implanted leads inside a human body. Specifically, this system can be used in electrical/optical stimulation/recording applications.

In some arrangements, the connector system is completely modular and easily expandable. These characteristics allow long term device trialing without causing significant discomfort, or at least reduced discomfort, to a patient in comparison with previous connector systems.

In some arrangements, a connector system according to the present teachings provides an external connector with a significantly lower profile. The external connector in some arrangements is made of flexible material that can conform to the skin of the patient.

In some arrangements, the in-line lead system is significantly smaller than alternative lead systems currently available. In some arrangements, the in-line lead system has between 10 and 50 contacts, and preferably between 22 and 32 contacts.

The connector system preferably can be used as an interface between any known medical external electrical stimulation and/or recording system and any medical implanted neural and/or muscular electrodes.

The invention claimed is:

1. A modular multi-channel inline connector system for connecting an implanted electrode within a body with a device, the system comprising:
    a first lead comprising the implanted electrode and a first connector portion;
    a second lead comprising a second connector portion, and operatively connected to the device, wherein the device is an external device located external to the body;
    wherein one of the first and second connector portions comprises a male connector and the other of the first and second connector portions comprises a female connector; and
    wherein the first and second connector portions are arranged to connect with each other and to be operatively located embedded within the body,
    wherein the female connector comprises an outer body in the form of an elongate tube having a first longitudinal axis extending from a first end of the elongate tube to a second end of the elongate tube, the elongate tube having an open end at the first end aligned with the first longitudinal axis, and one or more lead wires extending out of the outer body at the second end, wherein the one or more lead wires and the opening are aligned along the first longitudinal axis, and
    wherein the male connector comprises an elongate body having a second longitudinal axis, wherein the elongate body is slidably received into the elongate tube through the open end of the female connector along the first longitudinal axis; and
    wherein the male and female connector portions are lined with isolation pads that prevent body fluids from entering the male connector received in the elongate tube through the open end of the female connector and shorting the first and second leads whereby the male connector is received within the female connector so as to form a seal therewith;
    a third connector portion attached to the second lead, wherein the third connector portion comprises a plurality of male connectors; and
    a fourth connector portion coupled to the external device, wherein the fourth connector portion comprises a PCB base, a multi-pin connector operatively connected to the PCB base, and the PCB base defining a plurality of receiving slots
    wherein the third connector portion connects with the fourth connector portion located on the exterior of the body, and
    wherein at least one of the male connectors of the third connector portion is operatively received within at least one of the receiving slots of the fourth connector portion to operatively connect the implanted electrode with to the external device.

2. The system of claim 1, wherein the second lead comprises a plurality of percutaneous lead wires.

3. The system of claim 1, wherein the first lead comprises one or more implanted lead wires.

4. The system of claim 1, wherein the device comprises an implanted device.

5. The system of claim 1, wherein each of the male connectors comprises an elongate body having a longitudinal axis, a plurality of transverse grooves longitudinally spaced along the body, an electrical contact disposed within at least one of the grooves, and a lead wire connected to each electrical contact and extending through the body to the respective lead.

6. The system of claim 5, wherein each of the receiver slots of the fourth connector portion comprises:
    an elongate slot having an open top side extending along a longitudal axis of the elongate slot; and
    an open end at one longitudinal end of the elongate slot, wherein the body of a male connector of the third connector portion is slidably received into a corresponding receiving slot of the fourth connector portion through the open top side.

7. The system of claim 1, wherein the male connector comprises an alignment groove extending longitudinally along an outer surface thereof, and
    the female connector comprises a threaded screw hole extending through the body and aligned transverse to the first longitudinal axis, and
    wherein an anchor screw extending through the screw hole engages the alignment groove to guide the male connector along the first longitudinal axis as the male connector is inserted into the female connector and makes a tight, sealed contact between the female connector and the male connector.

8. The system of claim 7, wherein an anchor screw screwed into the threaded screw hole makes a tight, sealed contact between the male connector inserted into the female connector.

9. A modular multi-channel inline connector system for connecting an implanted electrode within a body with a device located external to or implanted within the body, the system comprising:
    a first lead operatively connected to the implanted electrode and to a first connector portion comprising a male connector;
    a second lead operatively connected to the device and to a second connector portion comprising a female connector;
    wherein the first and second connector portions are arranged to connect with each other to form a seal to prevent body fluids from entering the first and second connectors when connected and to be operatively located embedded within the body, wherein the female connector comprises an outer body in the form of an elongate tube having a first longitudinal axis, an open end at one end of the first longitudinal axis, a hollow channel at the second end of the outer body along the first longitudinal axis, and one or more lead wires extending out of the outer body of the female connector through the hollow channel at the second end of the outer body and along the first longitudinal axis, and a threaded screw hole extending through the outer body transverse to the first longitudinal axis, and wherein the male connector comprises an elongate body having a second longitudinal axis and includes an alignment groove extending longitudinally along an outer surface thereof and is slidably received into the elongate tube through the open end of the female connector, and wherein an anchor screw extending through the screw hole of the female connector engages with the alignment groove of the male connector to guide the male connector as the male connector is inserted into the female connector along the first longitudinal axis and makes a tight, sealed contact between the female connector and the male connector.

10. The system of claim 9, wherein each of the male connector and the female connector is lined with at least one silicone pad to form the seal.

11. The system of claim 10, wherein the device is an external device, and wherein the first lead comprises one or more implanted lead wires, and the second lead comprises a plurality of percutaneous lead wires.

12. A modular multi-channel inline connector system for connecting an implanted electrode within a body with an external device located external to the body, the system comprising:
 a first lead comprising the implanted electrode and a first male connector;
 a second lead comprising a first female connector and a second male connector, the first female connector having an outer body in the form of an elongate tube with a first longitudinal axis, a screw hole extending through the outer body transverse to the first longitudinal axis, and an open end at one end of the first longitudinal axis; and
 a second female connector operatively connecting the second lead to the external device;

wherein the first male connector comprises an elongate body having a second longitudinal axis and includes an alignment groove extending longitudinally along an outer surface thereof, wherein the male connector is slidably received into the elongate tube of the first female connector through the open end to operatively electrically connect with each other and to form a seal to prevent body fluids from entering the first male and female connectors when connected and to be operatively located embedded within the body, wherein an anchor screw extending through the screw hole of the female connector engages with the alignment groove of the male connector to guide the male connector as the male connector is inserted into the female connector along the first longitudinal axis and makes a tight, sealed contact between the female connector and the male connector; and wherein the second male connector connects with the second female connector on the exterior of the body.

13. The system of claim 12, wherein each of the first male connector and the second male connector comprises:
 an elongate body having a longitudinal axis extending between a first end and a second end, an enclosed interior channel extending along the longitudinal axis, a plurality of transverse grooves longitudinally spaced along an exterior of the elongate body, an electrical contact disposed within at least one of the grooves, and a lead wire connected to each electrical contact and extending through the interior channel body from the second end to the respective lead.

14. The system of claim 13, wherein the second female connector comprises an elongate slot having an open top side extending along a longitudinal axis and an open end at one longitudinal end of the elongate slot, and
 wherein the second male connector is slidably received into the receiving slot of the second female connector through the open top side.

* * * * *